United States Patent [19]
Moles

[11] Patent Number: 6,073,482
[45] Date of Patent: *Jun. 13, 2000

[54] FLUID FLOW MODULE

[75] Inventor: Donald R. Moles, Cedarville, Ohio

[73] Assignee: YSI Incorporated, Yellow Springs, Ohio

[*] Notice: This patent is subject to a terminal disclaimer.

[21] Appl. No.: 09/233,976

[22] Filed: Jan. 20, 1999

Related U.S. Application Data

[63] Continuation-in-part of application No. 08/897,744, Jul. 21, 1997, Pat. No. 5,932,799.

[51] Int. Cl.$^7$ .......................... G01N 11/00; F16K 31/145; C12M 1/40
[52] U.S. Cl. ...................... 73/53.01; 435/288.5; 251/61.1
[58] Field of Search .............................. 73/53.01; 422/56, 422/61; 435/288.4, 288.5, 288.7; 251/61.1, 331; 205/95

[56] References Cited

U.S. PATENT DOCUMENTS

| | | | |
|---|---|---|---|
| 3,912,614 | 10/1975 | Spracklen et al. | 204/195 B |
| 4,022,256 | 5/1977 | Berkman et al. | 141/1 |
| 4,187,883 | 2/1980 | Webster . | |
| 4,304,257 | 12/1981 | Webster | 137/559 |
| 4,312,332 | 1/1982 | Zick | 128/635 |
| 4,839,017 | 6/1989 | Taniguchi et al. | 204/403 |
| 4,848,722 | 7/1989 | Webster | 251/61.1 |
| 4,852,851 | 8/1989 | Webster | 251/61.1 |
| 4,858,883 | 8/1989 | Webster | 251/61.1 |
| 4,869,282 | 9/1989 | Sittler et al. | 137/15 |
| 4,894,253 | 1/1990 | Heineman et al. | 427/36 |
| 4,906,439 | 3/1990 | Grenner | 422/56 |
| 4,911,801 | 3/1990 | Pons | 204/59 R |
| 4,927,516 | 5/1990 | Yamaguchi et al. | 204/403 |
| 4,968,400 | 11/1990 | Shimomura et al. | 204/403 |
| 4,975,175 | 12/1990 | Karube et al. | 204/403 |
| 4,999,069 | 3/1991 | Brackett et al. | 156/84 |
| 5,017,494 | 5/1991 | Karube et al. | 435/288 |
| 5,041,181 | 8/1991 | Brackett et al. | 156/84 |

(List continued on next page.)

FOREIGN PATENT DOCUMENTS

| | | |
|---|---|---|
| 0368209 | 5/1990 | European Pat. Off. . |
| 394048A2 | 10/1990 | European Pat. Off. . |
| 0770871A2 | 5/1997 | European Pat. Off. . |
| 9002829 | 3/1990 | WIPO . |
| WO94/21386 | 9/1994 | WIPO . |
| WO95/08716 | 3/1995 | WIPO . |
| 9002357 | 1/1997 | WIPO . |
| WO97/02357 | 1/1997 | WIPO . |
| WO97/21090 | 6/1997 | WIPO . |

OTHER PUBLICATIONS

Selectivity and Sensitivity Improvements at Perfluorinated Ionomer/Cellulos Acetate Bilayer Electrodes; Joseph Wang and Peng Tuzhi, Dept. Of Chemistry New Mexico State University, Las Cruces, New Mexico 88003; Published in Alan. Chem. 1986, vol. 58, pp. 3257–3261.

International Search Report dated Nov. 5, 1998–PCT/US98/14950.

*Primary Examiner*—Hezron Williams
*Assistant Examiner*—Jay L. Politzer
*Attorney, Agent, or Firm*—Thompson Hine & Flory LLP

[57] ABSTRACT

Microfluidic analyzers are used to sense a plurality of analytes in whole blood, diluted blood, plasma or serum. Additionally in the rapidly growing fields of cell culture growth and fermentation, it is often necessary to measure glucose, glutamine, lactate, NH3, phosphate and iron in micro-scale fluid flow analysis systems. The present application is directed to a fluid flow module that allows for analyte sample flow therethrough while providing a site for the location of a sensing element or elements therein to detect analyte presence and/or concentration. The module is designed for microfluidic flow rates and volumes and can be discarded after use with simple replacement by another module.

14 Claims, 4 Drawing Sheets

U.S. PATENT DOCUMENTS

| | | | |
|---|---|---|---|
| 5,108,532 | 4/1992 | Thein et al. | 156/285 |
| 5,130,161 | 7/1992 | Mansur et al. | 427/38 |
| 5,138,881 | 8/1992 | Riley et al. | 73/304 R |
| 5,146,785 | 9/1992 | Riley | 73/313 |
| 5,213,675 | 5/1993 | Yamaguchi | 204/418 |
| 5,258,111 | 11/1993 | Karagozler et al. | 204/416 |
| 5,286,364 | 2/1994 | Yacynych et al. | 204/418 |
| 5,304,487 | 4/1994 | Wilding et al. | 435/291 |
| 5,376,252 | 12/1994 | Ekstrom et al. | 204/299 R |
| 5,401,376 | 3/1995 | Foos et al. | 204/415 |
| 5,407,992 | 4/1995 | Lee et al. | 427/523 |
| 5,411,765 | 5/1995 | Kanakarajan et al. | 427/385.5 |
| 5,421,982 | 6/1995 | Ikeda et al. | 204/414 |
| 5,442,030 | 8/1995 | Yang | 528/353 |
| 5,443,890 | 8/1995 | Ohman | 428/167 |
| 5,457,087 | 10/1995 | Dorothy et al. | 505/210 |
| 5,460,890 | 10/1995 | Okahashi et al. | 428/458 |
| 5,462,628 | 10/1995 | Viehbeck et al. | 156/281 |
| 5,468,374 | 11/1995 | Knoll | 210/96.2 |
| 5,470,644 | 11/1995 | Durant | 428/209 |
| 5,470,693 | 11/1995 | Sachdev et al. | 430/315 |
| 5,478,751 | 12/1995 | Oosta et al. | 436/165 |
| 5,486,335 | 1/1996 | Wilding et al. | 422/55 |
| 5,491,097 | 2/1996 | Ribi et al. | 436/518 |
| 5,505,321 | 4/1996 | Caron et al. | 216/20 |
| 5,520,788 | 5/1996 | Johnson | 204/415 |
| 5,525,405 | 6/1996 | Coverdell et al. | |
| 5,540,828 | 7/1996 | Yacynych | 204/418 |
| 5,543,222 | 8/1996 | Edman et al. | 428/335 |
| 5,554,339 | 9/1996 | Cozzette et al. | 422/50 |
| 5,567,297 | 10/1996 | Mertens et al. | 205/334 |
| 5,567,330 | 10/1996 | Dorothy | 216/18 |
| 5,578,188 | 11/1996 | Mertens et al. | 205/334 |
| 5,589,396 | 12/1996 | Frye et al. | 436/73 |
| 5,591,519 | 1/1997 | Caron et al. | 428/344 |
| 5,596,038 | 1/1997 | Subramaniam | 524/547 |
| 5,598,989 | 2/1997 | Ross et al. | 244/158 A |
| 5,603,820 | 2/1997 | Malinski et al. | 205/781 |
| 5,618,760 | 4/1997 | Soh et al. | 438/703 |
| 5,635,358 | 6/1997 | Wilding et al. | 435/7.2 |
| 5,637,469 | 6/1997 | Wilding et al. | 435/7.21 |
| 5,660,370 | 8/1997 | Webster | 251/129.17 |
| 5,660,728 | 8/1997 | Saaski et al. | 210/251 |
| 5,667,851 | 9/1997 | Edman et al. | 205/95 |
| 5,839,722 | 11/1998 | Berlin et al. | 271/265.02 |

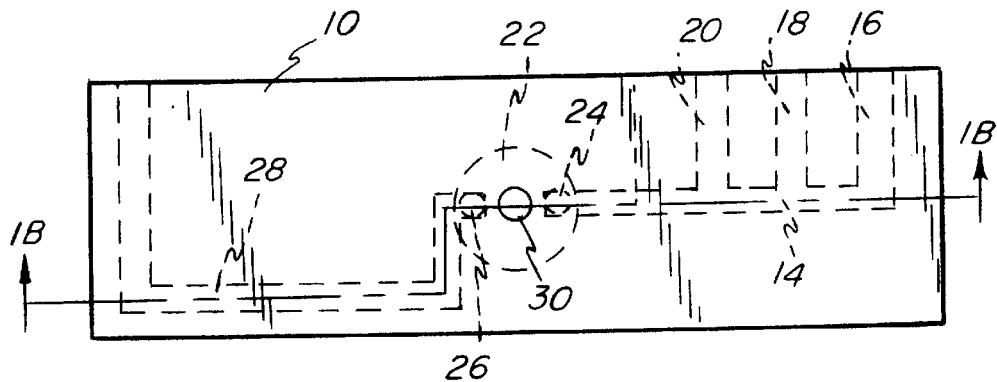
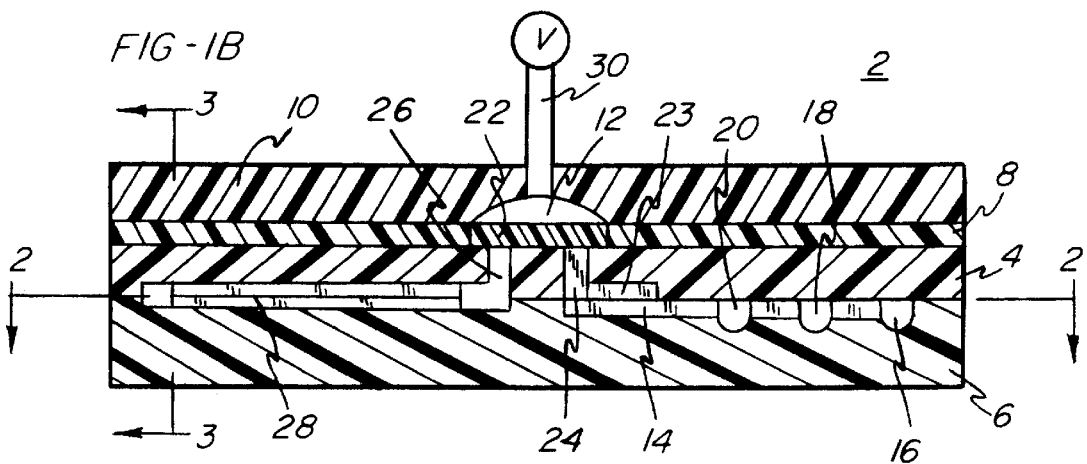
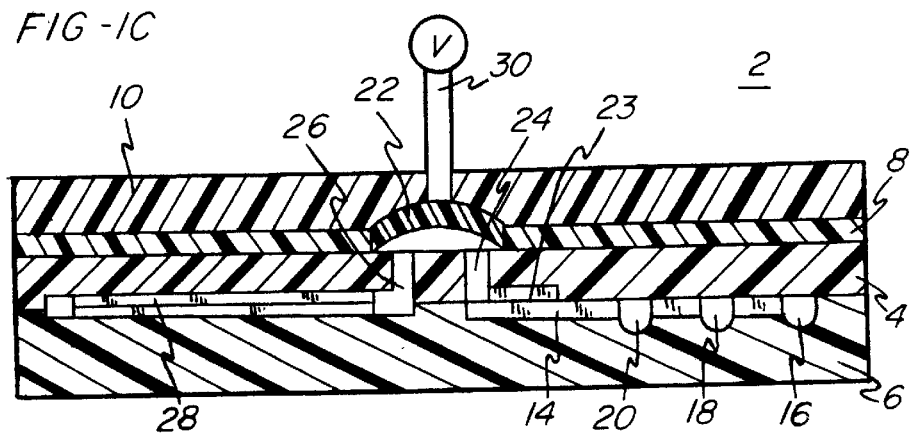

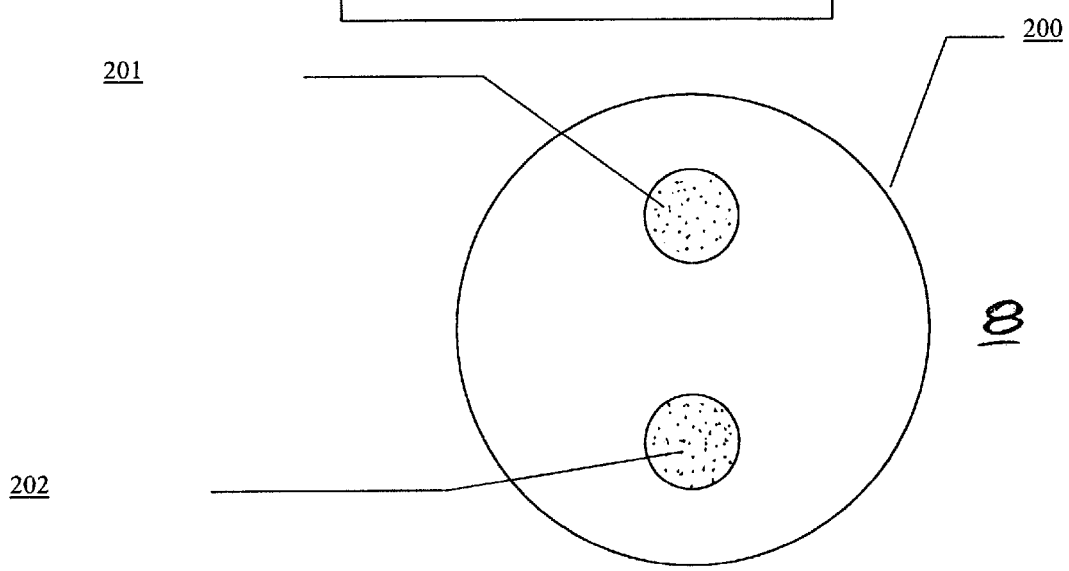

FLUID FLOW MODULE

CROSS-REFERENCE TO RELATED APPLICATIONS

This application is a continuation-in-part of U.S. Ser. No. 08/897,744 filed Jul. 21, 1997, now U.S. Pat. No. 5,932,799, Aug. 3, 1999.

FIELD OF THE INVENTION

The present application is directed to a fluid flow module that allows for analyte sample flow therethrough while providing a situs for the location of a sensing element or elements therein to detect analyte presence and/or concentration. The module is designed for microfluidic flow rates and volumes and can be discarded after use with simple replacement by another module.

BACKGROUND OF THE INVENTION

Microfluidic analyzers have been used to sense a plurality of analytes in whole blood, diluted blood, plasma or serum. Additionally in the rapidly growing fields of cell culture growth and fermentation, it is often necessary to measure glucose, glutamine, lactate, $NH^3$, phosphate and iron in micro-scale fluid flow analysis systems.

Due to the scarce and often expensive nature of the fluid medium containing the analyte, it is imperative that the fluid medium should be conserved with only the smallest amounts used for the analysis. Also, the emphasis toward insitu measurement of biological fluids such as cell culture media dictates that the analytical equipment should not only be small in size, but component parts of the analytical system should also be designed for easy removal from the system and rapid replacement of a new component part to the system so that cleanliness of the component can be accurately controlled without interruption in the monitoring effort. Moreover, such a component or assembly itself should be as free from contamination itself as possible.

There are several additional reasons why the measurement of sterile biological fluids benefit from the use of a disposable microfluidic; for the measurement of sterile fluids the measurement system should be enclosed, i.e. all wetted parts should be sealed so that they may be sterilized and remain that way during monitoring. If the entire fluidic system (including sensor, reagents and waste) is to be enclosed then economics dictate that it should be small, preferably very small.

Another aspect of the micro approach responds to the above-noted need to consume only small amounts of samples. If small amounts of sample are withdrawn for analysis then small conduits are needed to convey the sample to the analyzer in order to deliver a timely result. This can be accomplished in two ways: first the conduit should be small in diameter, secondly it should be as short as possible. The best way to keep the sample conduit short is to move the analyzer to the sample. The only practical way to accomplish this is to develop the analyzer and conduit on a micro scale.

SUMMARY OF THE INVENTION

The present invention is therefore directed to an easily assembled and manufactured microfluidic analyzer module that is adapted for easy interchangeability with a previously utilized module so that, if desired, the technician or scientist can disconnect the module and easily replace it with another. Additionally, the module itself is constructed of a plurality of directly bonded polymer layers in a sandwich laminate structure wherein the interfacial surface areas of the laminate have been etched or otherwise formed into a network of communicating microflow channels. Typically, the channels are trough-like recesses adapted for microfluid flow therein and may have widths of about 0.001–0.015" with channel depths being about 0.0005–0.015".

The module is preferably constructed of thin polymeric, laminate layers that are bonded together to form the laminate without the use of adhesives or glues that are normally used in adhesive bonding of laminate layers. This fact is especially important in critical analytical operations. Quite obviously, the presence of undesired contaminant molecules. especially those proximate the fluid containing channels, interferes with accuracy of the analytical determination.

The use of adhesives, because of the reduced scale involved. also compromises geometry. Adhesives, if liquid. tend to flow into channels, if dry, they tend not to be patternable which means that they can be mis-registered, which leads to voids along the channel or sensor cavities. These voids are "dead" volumes which destroy the desirable properties of the flow channel and make the behavior of the system less reproducible from system to system.

Further, the individual layers of the laminate can be subjected to high resolution microlithographic etching or other high resolution etching methods. When these layers are contiguously placed and bonded to each other in a sandwich construction they define a network of small or micro dimensioned channels with certain channel portions formed in a surface area of one laminate layer and other channel portions formed in the contiguous surface area of an adjacent laminate layer.

A thin, polymeric valve layer is also provided as part of the laminate structure. The valve layer is securely bonded over the sandwich construction over all surface areas except those in which valving action must occur. That is, in those areas of the sandwich in which valving action is needed to selectively block or open communication between channels of the network, an overlying flexible polymer valve is provided with flexing of the polymer valve against the underlying laminate layer surface functioning to open or block channel communication.

In accordance with the invention, complex three dimensional structures can be constructed from layers, with the benefit that each layer can be treated as a planar, two dimensional, entity. This is significant because of the extensive capabilities which have been developed which support the micromachining of planar substrates. The ability to build these layers into three dimensional structures requires not only bondability but the use of techniques of registration and bonding which preserve the integrity of the micro features themselves.

The materials used to form the module are inert, micromachinable, bondable and dimensionally stable. Additionally, metal layers may be readily provided over these materials. This is an important consideration in regard to the desirable integration of sensor and fluidic.

In accordance with a preferred embodiment of the invention, the module, in its simplest form, is fabricated from a valve layer and a pair of channel bearing layers and these layers are formed from self-bondable polyimide sheets. The invention also provides a method for fabricating the module using self-bondable polyimide sheets wherein the channel bearing layers and the valve layer are assembled and directly interfacially bonded to is one another using heat and pressure as described in more detail herein. In accordance with the invention, in order to prevent the valve layer from bonding to the channel bearing layer in the valve region, a release agent is applied in this region. The release agent is preferably applied to the surface of the channel bearing layer adjacent the valve layer, but the release agent could be applied to the corresponding valve region of the valve layer instead of or in addition to applying the release agent to the valve region of the channel bearing layer. The release agent can be applied using sputter deposition techniques.

The invention will be farther described in conjunction with the appended drawings and following detailed description.

SUMMARY OF THE INVENTION

FIG. 1A is a plan view of a microfluidic analyzer module in accordance with the invention;

FIG. 1B is a sectional view of the microfluidic analyzer module shown in FIG. 1A taken along the plane represented by the lines and arrows 1B—1B thereof;

FIG. 1C is a sectional view of the microfluidic analyzer module similar to that shown in FIG. 1B, but here showing positioning of the valve member in the open position to allow communication between certain channels of the fluid network;

FIG. 7 is a plan view of the surface of a polyimide sheet 4 which has been spot treated with a release agent in the valve region.

DETAILED DESCRIPTION OF THE PREFERRED EMBODIMENT

Figure 2:
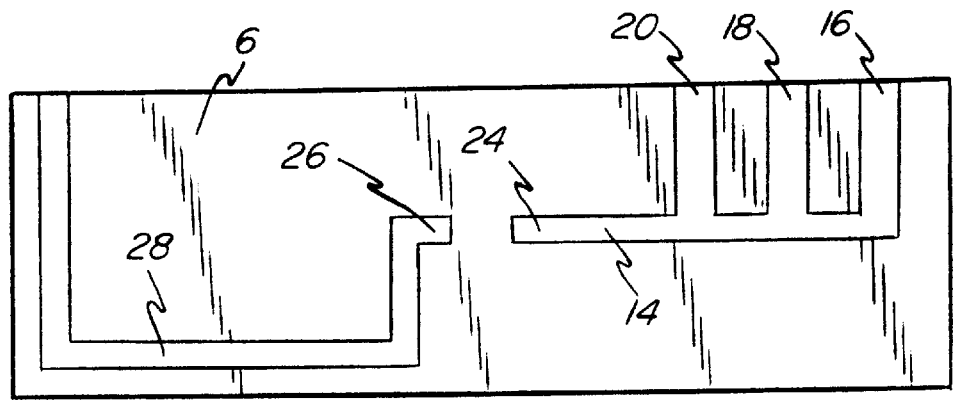
FIG. 2 is a sectional view of the microfluidic analyzer module taken along the plane represented by the lines and arrows 2—2 of FIG. 1B.

Turning now to FIGS. 1A and B of the drawings, there is shown a microfluidic analyzer module 2 of the present invention comprising an upper polymer layer 4 superposed over lower polymer layer 6. As shall be explained later, the layers 4 and 6 are channel bearing layers in that they will be etched or otherwise provided with channels or portions of channels therein. Upon mating of the layers 4, 6 in superposition, a channel network is formed. A polymeric valve layer 8 is disposed on top of the layer 4 so as to selectively open and shut fluid ingress and egress channels to allow fluid flow therebetween and through the module.

As shown. lower polymer layer 6 is provided with an inlet channel 14 therein which, may be formed by suitable methods such as microlithographic etching techniques including wet, plasma, laser or e-beam etching or the like. Additionally, the channels may be formed via mechanical methods such as milling, scribing or high pressure particle stream methods. The inlet channel 14 comprises respective feed channels 16, 18, 20, in this case provided for feed of calibrant, buffer and analyte solutions to the inlet channel 14 of the analyzer module.

Upper polymer layer is provided with inlet channel 24 which is partially positioned over channel 14. This channel communicates with perpendicularly disposed inlet channel 24 which extends perpendicularly through the layer 4 and is positioned adjacent valve egress channel 26 which, in turn communicates with sensor channel 28. The lower portion of channel 28 is formed in the lower polymer layer.

Fluid flow between the inlet channel 24 and valve egress channel 26 is selectively controlled via movement of valve member 22 which is an integral part of valve layer 8. The valve 22 surrounds the area adjacent the bores communicating with inlet and egress channels 24, 26 respectively, which bores are perpendicularly disposed with regard to and terminate in the top planar surface of upper polymer layer 4. A valve support layer 10 constructed of rigid plastic such as polyethylene, polypropylene, polycarbonate or polyphenylsulfone is provided on top of the upper polymer layer 4. The valve support layer 10 includes a vaulted concavity 12 which is positioned directly on top of the valve 22.

In one possible mode of operation a valve actuation conduit 30 is provided so that pneumatic or hydraulic fluid in communication with the conduit will selectively apply negative or positive pressure to the conduit thereby opening and closing the valve 22. In other words, valve 22 in its open position will flex so that it will be arched upwardly in the concavity 12 (see FIG. 1C) thereby allowing fluid communication between the inlet channel 24 and valve egress channel 26. Conversely, when positive pressure is applied through the conduit 30, the valve 22 will return to a position wherein it is contiguous with the top surface of upper polymer layer 4 (FIG. 1B), thereby closing communication between the inlet 24 and egress channel 26.

In the preferred method of operation, the fluid pressure will open the valve. In this way instantaneous negative pressure is not applied to the channel fluid which can cause degassing and the creation of bubbles. Bubbles are of course very undesirable in a microfluidic due to the surface tension of the bubble and the channel wall and the resulting increase in the resistance to channel flow.

It is noted that the interfacial areas defining boundaries between the upper polymer layer 4 and lower polymer layer 6 are directly bonded together without any adhesive. Also, the polymer valve layer 8 is directly bonded to the upper layer 4 without an adhesive means in all of those interfacial regions between layers 4 and 8 save for the valve areas 22. Accordingly, considerable flex and stretch remains in the valve area 22 so that the flexible polymer in this area may be free to flex upwardly toward the vaulted concavity 12 to open the valve and thereby provide communication between inlet 24 and egress channel 26.

Turning now to FIG. 2, there is shown lower polymer layer 6 and inlet channel 14 formed therein. Inlet channel 14 communicates respectively with calibrant branch feed channel 16, buffer feed branch channel 18, and analyte branch feed channel 20. Sensor channel 28 is in communication with valve egress channel 26.

Figure 3:
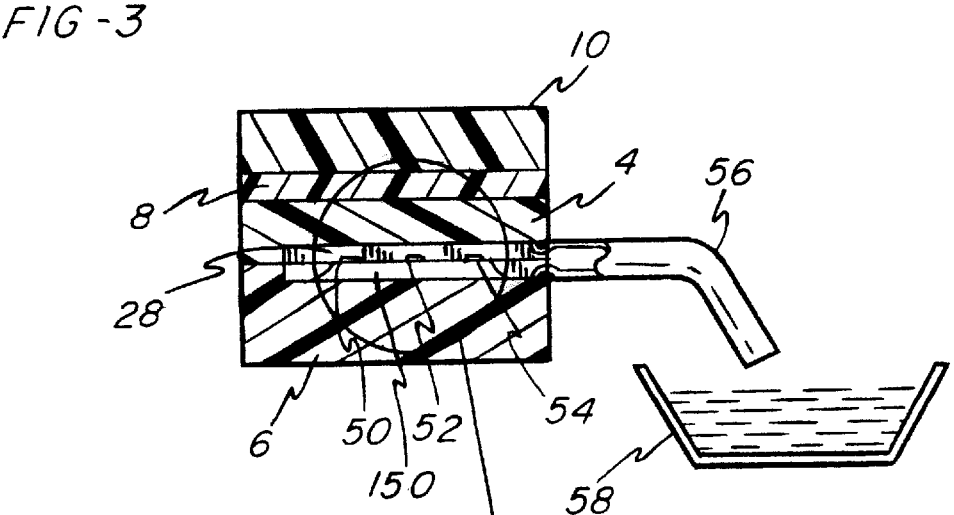
FIG. 3 is a sectional view taken along the plane represented by the lines and arrows 3—3 of FIG. 1B.

Turning now to FIG. 3, Sensor channel 28 is provided in the lower surface of upper polymer layer 4 and upper surface of layer 6. As shown in the drawing, the fluid to be analyzed passes from left to right and is in fluid flow contact with reference electrode 50, working electrode 52, and counter-electrode 54, which are formed along the sensor channel. As the fluid flows from left to right and passes over the electrodes, it flows to outlet conduit 56 and into tank 58. The outlet conduit 56 can be connected to channel 28 via snap or other quick connect mechanism to facilitate easy removal and replacement of the module 2.

Figure 3A:
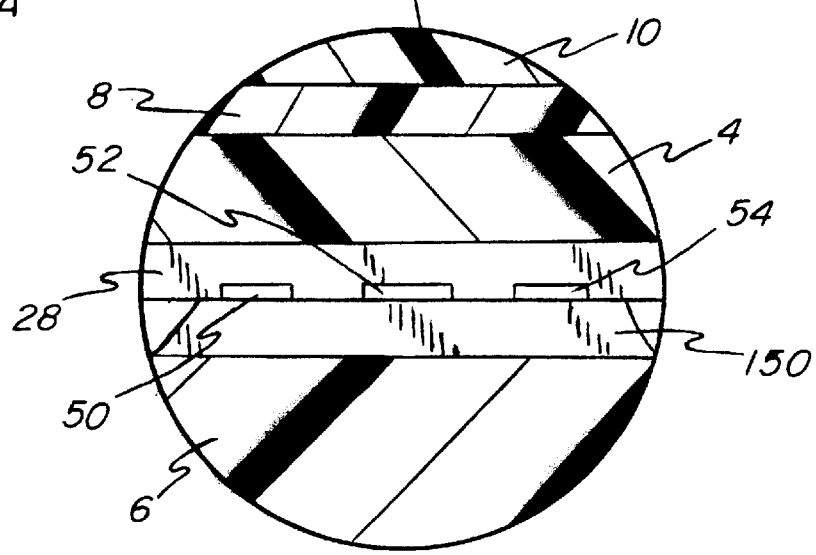
FIG. 3A is a magnified view of a portion of FIG. 3 showing the disposition of the sensor electrodes in the sensing channel.

As may best be seen in the magnified view, FIG. 3A, the electrodes are positioned on a plateau region 150 corresponding to the top surface of lower layer 6 within the sensor channel 28. This is accomplished by allowing a half-channel step in the sensor channel in the region of the electrodes.

It is to be remembered that although a specific electrode structure is shown in FIG. 3, other sensors could similarly be employed to contact the fluid flowing through the sensor channel. In this regard, other electrochemical or even optical sensors may be suitably disposed within sensor channel 28, in order to sense the presence or concentration of an analyte, all within the gambit of the present invention.

Figure 4:
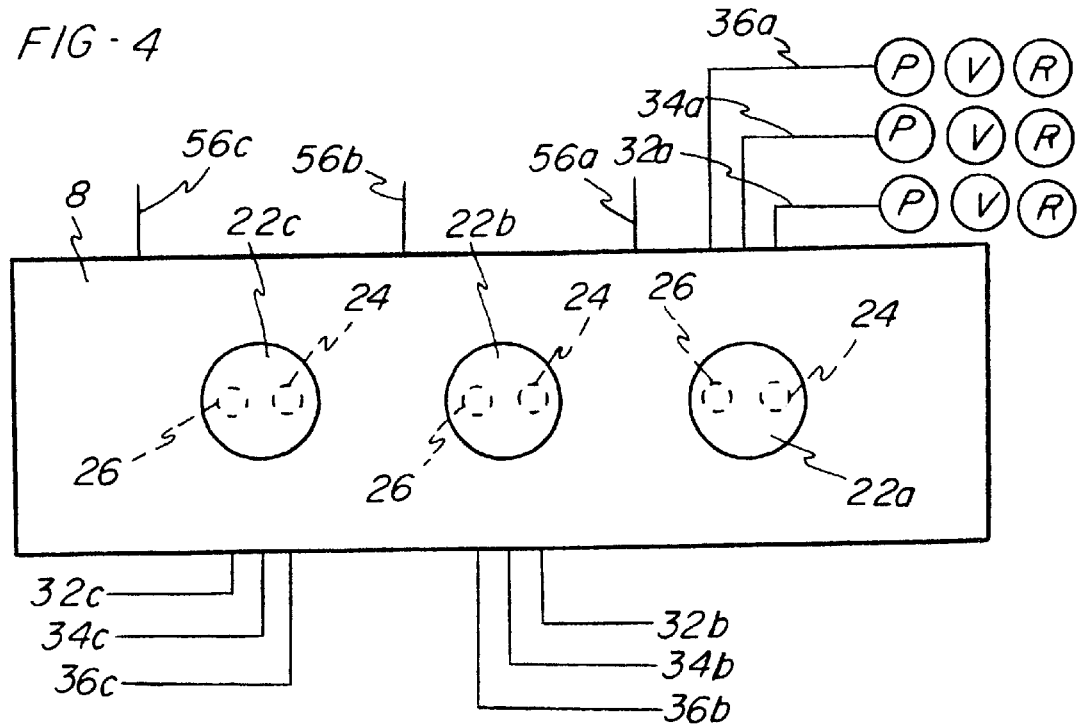
FIG. 4 is a diagrammatical section view of another microfluidic flow analyzer module taken through a plane represented by the valve layer thereof which valve layer is disposed similarly to the valve layer disposition shown in FIG. 1B.

Turning now to FIG. 4, there is shown a sectional view of another microfluidic flow analyzer module in which a plurality of fluid flow cells are provided. Each cell is defined as including feed channel means, sensor channel means, and a valve for selectively blocking or allowing communication between the feed and sensor channels. The embodiment shown in FIGS. 1A–3 depicts a microfluidic flow analyzer module having one cell. However, in many commercial applications it will be desirable to provide a multi-cell module so that, for example, each cell may provide for analysis of a different analyte. Here, valve layer 8 includes valve areas 22a, b, and c. Underlying each area 22a, b or c are a pair of perpendicularly extending inlet and egress channel means similar to the members 24, 26 shown in FIG. 1. Each of these members terminates in a bore in the planar top surface of upper polymer layer 4. Additionally, in FIG. 4. feed conduit means have been shown for each cell and include calibrant conduits 32a, b, c, buffer conduits 34a, b, c, and analyte conduits 3a, b, c each with its associated pump, valve and reservoir. Additionally, three outlet conduits 56a, b, and c are shown, each one associated with one of the cells. A microfluidic flow analyzer module in accordance with the invention may contain a multiplicity of feed and sensor channels with each cell performing one or a variety of analyte sensing functions.

For each cell shown in FIG. 4, the feed channel 14 thereof is provided with feed conduits 32a, b or c, 34a, b, or c, 36a, b or c. These conduits are snap or otherwise matingly engaged with respective branch feed channels 16, 18, 20 (such as those shown in FIG. 1A) so that the module 2 can be readily disconnected from the analytical system and replaced with another module 2. For each of the feed conduits 32a, b or c, 34a, b or c, 3a, b or c, pumps P are provided and may be operated for example by solenoid actuation through microprocessor control. The pumps include well known peristaltic pumps that are designed to pump a metered quantity of fluid from the reservoir R connected to the pumps P by valving mechanisms V. Additionally, each of the sensor channels 29 (see FIG. 3) are operatively connected to an outlet conduit 56a, b, or c via quick connect fittings. Again, this facilitates rapid replacement of one module 2 with another.

Although external pumps, valves and reservoirs are shown in the drawings and described herein above for purposes of clarity and simplification, it is thought that virtually all micro fluid handling processes can be accommodated within the confines of the planar interfacial surfaces of the layers 4, 6 or 4, 8. It is presently envisioned that pressurized fluid reservoirs will be used in conjunction with restrictive membranes to accomplish the desired reagent microflow.

As indicated above, any sensing means may be utilized and substituted for the electrodes 50, 52, 54. The only criterion is that the sensor, including electrochemical and optical sensors, should be capable of measuring the analyte as it flows past the sensing element in the sensor channel of the microfluidic flow analyzer module.

Additionally, multiple analysis can be conducted in one channel by in-line series disposition of multiple sensor elements along the channel. In those cases in which electrodes such as those 50, 52, 54 are shown, they may be deposited on the plateau region 150 of the sensor channel by photo patterning, screen printing, ink jet, or micro-syringe type methods. Further, the electrodes could be covered by one or more enzyme containing membranes and interference rejection membranes if desired. In the case in which enzymes or other sensing elements are to be disposed adjacent the electrode, these can be immobilized in a polymeric medium. The polymeric medium may be electropolymerized over the electrode by, for example, the methods reported in U.S. Pat. Nos. 5,540,828 and 5,286,364 to Yacynvch.

The microfluidic flow analyzer module in accordance with the invention can be utilized in conjunction with a plurality of different sensing methods including electro-chemical amperometric, potentiometric, or conductimetric methods. Additionally, optical sensors can be utilized in conjunction with the invention to detect fluid motion as well as analyte concentration, although the primary concern is to provide an amperometric glucose sensor for fermentation and cell culture media. One of the advantages of using self-bondable polyimide sheets in fabricating the module is that these sheets are relatively clear optically and thus facilitate the use of optical sensors. Additionally, other analytes such as glutamine, lactate, and ammonia can be sensed using the modules of the invention.

In the specific embodiment shown herein in FIGS. 1A–3, the auxiliary electrode may comprise platinum that is deposited via sputter coating, e beam evaporation or other methods. The working electrode will comprise platinum, deposited as stated above, and this electrode may be covered with an enzyme-containing laminated structure of the type known in the art. Finally, the reference electrode may comprise silver that is deposited by sputter coating followed by a chloridizing treatment to form a silver/silver chloride reference electrode. The reference electrode may also be formed using a platinum base over which a silver plated film is formed followed by chloridizing.

The feed and sensing channels formed in the upper and lower polymer layers of the analyzer module may be formed in the requisite surface portions of the upper and lower polymer layers by etching via photo developed micro-lithographic patterns. For example, a suitable photo resist will be applied to the substrate and then the surface of the substrate will be aligned with a mask followed by exposure to, for example, UV radiation. The etching of the polymer coating and developing of the photoresist can be accomplished in one step with a dilute aqueous alkaline solution when a positive photoresist is used. Typical etchants are dilute solutions of NaOH, KOH, tetra-alkali ammonium hydroxide, etc. The surface is then neutralized and rinsed for example with immersion in acidic acid followed by rinsing in DI water. The photoresist can be stripped with solvents such as acetone, butyl acetate or higher acetates. The skilled artisan will be able to fashion whether a positive photoresist or a negative resist should be used and the particular types of photo resists that can be applied. Also, etching of the desired pattern may be accomplished via normal high resolution techniques including electron beam, laser or ion beam etching.

The polyimides are preferred for use as the layers 4, 6, and 8. These polymers are available commercially in thin film form with desirable film thicknesses being on the order of about 0.5–30 mils. So that the films may be bonded without application of adhesives and the like between layers, it is most desirable to employ self-bondable polyimides as the layers 4, 6, and 8. Suitable adhesiveless directly bondable polyimides are reported in U.S. pat. No. 5,525,405 (Coverdall et al.). The disclosure of this patent is incorporated by reference herein.

As is reported in the '405 patent, multiple polyimide film layers may be superimposed on and directly bonded to each other without use of an adhesive. These directly bondable polyimides are aromatic polyimides containing from about 400–10,000 parts of an inorganic bonding enhancing agent such as Sn. The films comprise the polymerization—imidization product of an aromatic tetracarboxylic dianhydride component and an aromatic diamine component.

The aromatic polyimides are commonly prepared via reaction of an aromatic dianhydride and an aromatic diamine in an organic solvent medium. This results in formation of a soluble polyamic acid. This reaction normally proceeds at room temperature and is slightly exothermic. The polyamic acid precursors are converted to polyimides by dehydration, using heat or reagents such acetic anhydride or pyridine.

The most popular commercially available polyimide films are formed by the condensation reaction of pyromellitic dianhydride (PMDA) and oxydianihine (ODA). The reaction is illustrated in the following scheme:

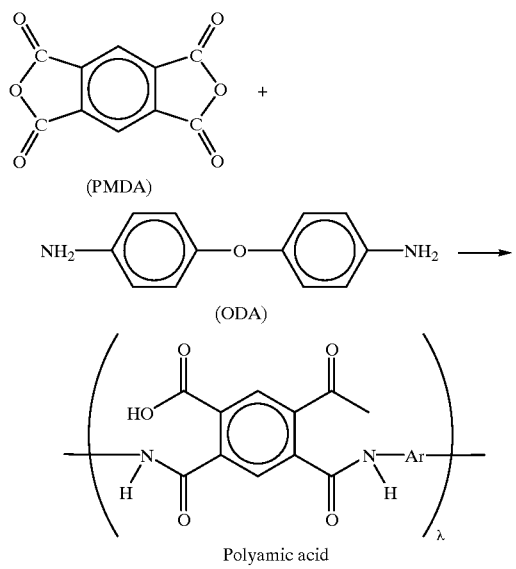

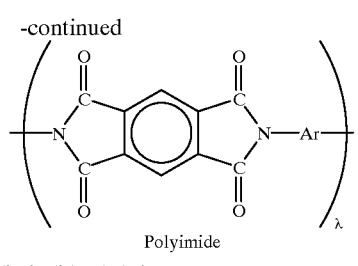

Polyimide

Ar = oxydianiline (i.e. 4,4'-diaminodiphenyl ether)

As is stated in the '405 patent a host of other aromatic dianhydrides and aromatic diamines can be used. Suitable dianhydrides for use in the polyimide films include: pyromellitic dianhydride; 2,3,6,7-napthalene tetracarboxylic dianhydride; 3,3',4,4'-biphenyl tetracarboxylic dianhydride; 1,2,5,6-napthalene tetracarboxylic dianhydride; 2,2',3,3'-biphenyl tetracarboxylic dianhydride: 3,3',4,4'-benzophenone tetracarboxylic dianhydride; 2,2-bis(3,4-dicarboxyphenyl) propane dianhydride; 3,4,9,10-perylenetetracarboxylic dianhydride; 1, 1-bis(2,3 dicarboxyphenyl) ethane dianhydride; 1, 1-bis(3,4-dicarboxyphenyl) ethane dianhydride; bis(2,3-dicarboxyphenyl) methane dianhydride; bis(3,4-dicarboxyphenyl) methane dianhydride; oxydiphthalic dianhydride; bis(3,4-dicarboxyphenyl) sulfone dianhydride; and the like.

Suitable aromatic diamines for use in the polyimide films include: 4,4'-diaminodiphenyl propane; 4,4'-diaminodiphenyl methane; benzidine; 3,4'-dichlorobenzidine; 4,4'-diaminodiphenyl sulfide; 3,4'-diaminodiphenyl sulfone; 3,4'diaminodiphenyl sulfone; 4,4'-diaminodiphenyl ether; 3,4'-diaminodiphenyl ether; 1,5-diaminonaphthalene; 4,4'-diaminodiphenyl ethyl phosphine oxide; 4,4'-5diaminodiphenyl N-methyl amine; 4,4'-diaminodiphenyl N-phenylamine; 1,4-diaminoberizene (p-phenylene diamine); 1,3-diaminobenzene; 1,2-diaminobenzene; and the like.

As mentioned in the '405 patent, copolyimides can also be prepared from the above precursors. Specifically mentioned are copolyimides derived from 15–85 mole % biphenyl tetracarboxylic dianhydride, 15–85 mole % pyromellitic dianhydride, 30–10 mole % p-phenylenedramine and from 0–70 mole % 4,4'diaminodiphenyl ether. The following copolymer is mentioned as preferred:

30 mole % pyromellitic dianhydride
20 mole % 3,3',4,4'biphenyltetracarboxylic dianhydride
30 mole % p-phenylene diamine
20 mole % 44'-diaminodiphenyl ether The '405 patent indicates that the organic solvents include normally liquid N, N-dialkylcarboxylamides, generally. Preferred solvents include the lower molecular weight members- of such carboxylamides, particularly N,N-dimethylformamide and N,N-dimethylacetamide. Other solvents which may be used include dimethylsulfoxide, N-methyl-2-pyrrolidone, tetramethyl urea, dimethylsulfone, hexamethylphosphoramide, tetramethylene sulfone, and the like. The amount of solvent used preferably ranges from 75 to 90 weight % of the poly(amid acid), since this concentration has been found to give optimum molecular weight.

The solvated poly (amic) acid is further condensed to form the desired polyimide via heating at temperatures ranging from about 50° C. initially, followed by higher temperature heating of about 350–400° C. to result in almost complete condensation of the polyamic acid intermediate to the imide form.

So as to enhance the adhesive-less bonding properties of the films a metallic bond enhancing agent such as Sn is added to the polyimide during the polymerization or film forming process. As reported in the '405 patent, Sn in the amount of about 400–10,000 ppm has proven effective. Reputedly, the preferred amount of Sn ranges from 1,000–4,000 ppm with the most preferred amount being about 1,200–3,500 ppm. Tin can be added as an organotin compound as described in U.S. Pat. No. 5,272,194 or a $Sn^{+2}$ or $Sn^{+4}$ salt as specified in U.S. Pat. No. 5,218,034. Bistributyltinoxide is mentioned as a preferred organotin compound.

In accordance with the invention, the layers 4, and 6 of the microfluidic flow analyzer module are preferably composed of DuPont® NA™ Kapton® polyimide film (formerly known as "DuPont XNA™ Kapton® polyimide film). This is a film of thermoset polyimide available and advertised as an adhesiveless, self-bondable film. The preferred film thickness is 5 mils.

With regard to the valve layer 8 in accordance with the invention, preliminary investigation indicated that this can be composed of DuPont's Kapton® KJ thermoplastic polyimide film. The preferred thickness for this film is about 1 mil. In accordance with a preferred embodiment of the invention, the layer 8 is composed of an adhesiveless, self-bondable polyimide film such as DuPont® NA™ Kapton® film. The preferred thickness of this film is 0.5 mils. The use of self-bondable polyimide film in the valve layer as well as the polymer layers 4 and 6 is advantageous because it yields a monolithic structure in which the valve layer is integrated with the underlying polymer layers except in the valve regions which are free to flex and thereby be opened and closed as described herein.

After the layers 4 and 6 have been purchased or prepared, the lower surface of layer 4 and top surface of layer 6 are etched in accordance with conventional techniques, as stated above, to provide the required pattern which will correspond to the sensor and feed channels in the finished microfluidic flow analyzer module. The perpendicularly arranged (i.e. with respect to the surface plane) channels 24, 26 can be inserted via conventional techniques including wet, plasma, E-beam, laser drilling or similar operations. The sensor means, such as electrodes, etc. can be placed along one of the layer surfaces defining a portion of the sensor channel 28. The layers 4, 6 are then placed in superposed relation with the etched surfaces thereof in mating, interfacial engagement to define the fluid flow channels needed for fluid inlet and outlet from the feed channel through the sensor channel.

Layer 8, the valve layer, can be processed to create through features using any of the above mentioned techniques. In addition to these methods the valve layer may be die cut, this being the preferred method.

The bonding operation may be performed by any of three methods, all of which incorporate the combination of heat and pressure. The autoclave method utilizes the pressures created by a liquid heated beyond its boiling point in an enclosed space. The materials to be laminated are placed within a bag which is then sealed after having been evacuated. The forces of the expanding vapor inside the confines of the autoclave exert pressure upon the bag surface thereby creating the conditions needed for bonding. The heated press method utilizes a heated platen in combination with a hydraulically, or otherwise mechanically, driven press to create the needed conditions. Yet another preferred method uses a high temperature oven in combination with a pressing fixture to accomplish bonding. In this method of bonding the materials to be bonded may be stacked in registration between two stiff metal platens which are connected to each other via a plurality of bolts, which, after tightening, hold the platens from moving apart from one another. This assembly then can be put inside an oven which is then heated to the required bonding temperature under which circumstances the differential expansion of the polymer layers versus the metal press components causes extensive pressure to be exerted upon the lamina inside the metal platens, sufficient to cause bonding of the layers.

Figure 5:
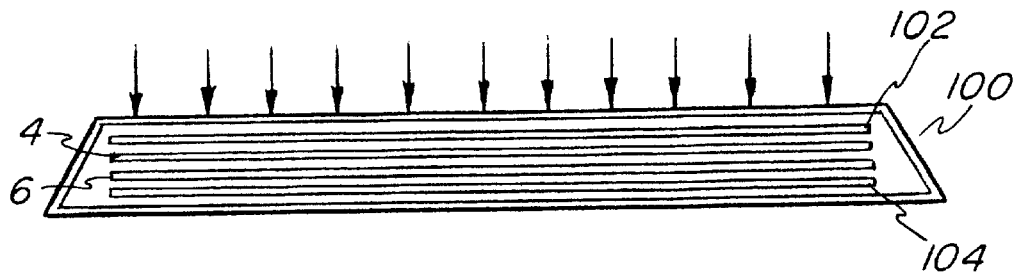
FIG. 5 is a schematic view of a press bonding autoclave that may be used in accordance with the invention to pressure bond layers of the microfluidic analyzer module.

As illustrated diagrammatically in FIG. 5, the appropriate layers are placed in a autoclave 100 or similar hot press apparatus. As shown, upper platen 102 is placed on top of the layers in the autoclave with lower platen 104 on the bottom. The platens may be hydraulically driven together to form a pressure nip on the layers.

The bonding operation may, be carried out in the autoclave, or other bonding apparatus, at temperatures of around 350–455° C. for DuPont NA™ material and at pressures of about 24–690 bar for a period of about 5 minutes to three hours. Process conditions for the DuPont KJ™ type material require about 275–350° C. at pressures of at least 14 bar for similar time periods. If heated press or oven methods are used then preferably, the heat-press bonding operation is carried out under vacuum of less than 760 mm Hg at the temperatures defined above appropriate to the material involved. In this manner the sandwich construction is formed.

If DuPont KJ™ is used as the material for layer 8, the valve layer, then bonding of the three layers 4, 6 & 8 must be performed in two bonding steps. First, using any of the three bonding techniques described above, layers 4 & 6, having been brought into registry, are bonded. Then, using the bonding parameters appropriate for the DuPont KJ™ material, the valve layer is bonded to the laminate constructed in the previous step. Accordingly, after the sandwich construction of layers 4, and 6 is provided, the valve layer 8 can be laminated over the top of the sandwich construction, again in a autoclave as shown in FIG. 5 or in another hot press.

Figure 6:
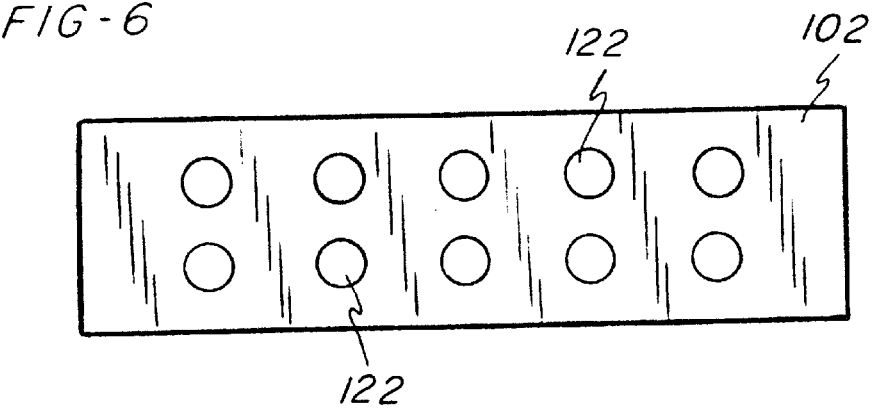
FIG. 6 is a plan view of a platen that may be used to pressure bond the valve layer over the channel containing layers of the microfluidic analyzer module.

Notably, when bonding the layer 8 of type DuPont™KJ to the sandwich assembly 4, 6, relief areas or apertures 122 are provided at least in the top platen 102 (as is depicted in FIG. 6). This platen (as well as the platens used in forming the original sandwich) has length and width dimensions that roughly match the dimensions of the layers 4,6, 8. However, during the bonding of the valve layer 8 to the sandwich, the relief areas 122 overlie the valve areas 22 that will appear in the finished module. During the pressing operation, less pressure will be exerted on the laminate in the areas 122 than along the other laminate areas under the solid portions of the platen. Accordingly, the layer 8 in those areas will not readily bond to layer 4 in the valve areas. The layer 8 in those areas will remain moveable and flexible so that ii will perform as a valve that upon actuation will selectively open and close communication between inlet channel 24 and valve egress channel 26. Additionally, the relief areas may be provided with vents so as to prevent build up of gas pressure from outgas products.

If, as is preferred, DuPont NA™ is used as the material for layer 8, the valve layer, then bonding of the three layers 4, 6 & 8 may be performed in one bonding step. Using any of the three bonding techniques described above, layers 4, 6 &, 8 having been brought into registry, may be bonded using the bonding parameters appropriate for the DuPont NA™ material. In this, the preferred embodiment of the invention, valve formation is accomplished by spot application of a thin-film release layer onto the upper surface of layer 4 in the vicinity of the valve, where it is desired that the valve film layer 8 remain flexible after construction. FIG. 7. shows a typical placement of the release material 200 in the valve region where the release material circumscribes the valve port openings 201, 202. The release agent prevents the valve layer 8 from bonding to the channel forming layer 4. The currently preferred release agent to be patterned is aluminum oxide in the chemical form $Al_2O_3$ but those skilled in the art will recognize other release agents could be used. Preliminary work indicates that the release agent should be applied in a thickness of at least about 400 Angstroms. The preferred method of deposition is radio-frequency sputtering under high vacuum conditions, although it may be applied using many other techniques known to those skilled in the art. In order to prevent thermal deformation of the polyimide sheet and the mask during sputter deposition it has been found desirable to place the sheets on a carousel and to rotate them through the RF generated discharge.

While the invention is illustrated in FIG. 7 with application of the release agent to the layer 4, those skilled in the art will recognize that the release agent could be applied to the corresponding portion of the valve layer 8. However, this is considered less desirable because the valve layer is typically a very thin film and consequently more difficult to handle. The presence of the film of the release agent on the valve layer may also be undesirable because it may make the diaphragm valve less flexible. Nevertheless, while spot application of the release agent to the valve layer may not be preferred, it is anticipated there may be constructions in which it would be feasible.

In this preferred method of construction, the placement of this release agent in the vicinity of the valve before bonding allows for the use of a completely smooth, unrelieved platen to be used in the pressing of the layers simultaneously. In this case the use of relieved platens would be disadvantageous since to do so would discourage bonding of channels, or other features within layers 4 and 6 which might lie under the relieved region of the platen, having thus, no pressure applied by the platen in these regions.

After the laminate consisting of layers 4, 6, and 8 is provided, the valve support layer 10 is bonded thereover by conventional means such as by use of a dry sheet adhesive or heat bonding of thin elastomer sheet in a liquid solvent medium. The microfluidic analyzer module comprising layers 4, 6, 8 and 10 can then, if desired, be mounted on a base or other mounting mechanism ready for insertion as a component of a fluid analysis system. The base may be attached/sealed to the module 2 using conventional means such as self-sticking double sided adhesive, heat-bondable sheet adhesive or through the use of an elastomeric gasket seal in combination with a glue or solvent applied to the perimeter of the rigid base and receiving structure.

The preceding description and accompanying drawings are intended to be illustrative of the invention and not limited. Various other modifications and applications will be apparent to one skilled in the art without departing from the true spirit and scope of the invention as defined by the following claims.

What is claimed is:

1. A module having fluid flow channels therein in fluid communication with a diaphragm valve, said module, comprising first, second and third interfacially superposed sheets of adhesiveless self-bondable thermoset polyimide directly bonded to one another without an adhesive, at least one fluid flow channel formed at the interface of said first and second sheets, said fluid flow channel being in fluid communication with a valve region on an outer surface of at least one of said first and second sheets, said third polyimide sheet being superposed over said valve region, the portion of said polyimide sheet overlying said valve region being capable of functioning as said diaphragm valve.

2. The module of claim 1 wherein said polyimide sheets contain an organotin compound.

3. The module of claim 1 wherein said third polyimide sheet is sufficiently flexible that the portion of said sheet overlying said valve region is capable of functioning as a valve and said third sheet is bonded to said outside surface except at said valve region.

4. The module of claim 1 wherein said module additionally includes a valve actuator operatively associated with said third polyimide sheet at said valve region for selectively flexing said sheet and thereby opening and closing said valve.

5. The module of claim 1 wherein said module includes a feed channel, a sensor channel, and valve regions operatively associated with said feed channel and said sensor channel for selectively opening and closing communication between said feed channel and said sensor channel, and a sensor disposed in said sensor channel to detect the presence or concentration of an analyte in said sensor channel.

6. The module of claim 1 wherein said first, second and third polyimide sheets are bonded together without an adhesive to form a monolithic structure.

7. The module of claim 5 wherein said feed channel includes a feed channel bore extending upwardly through said first polyimide sheet and terminating at the outer surface of said first polyimide sheet, a sensor channel bore extending upwardly through said first polyimide sheet and terminating at said outer surface of said first polyimide sheet approximate said feed channel bore, said valve region extends over said feed channel bore and said sensor channel bore and a valve actuator for pressing said third polyimide sheet over said feed channel bore and said sensor channel bore to block communication therebetween and for relaxing said third polyimide sheet for opening communication therebetween.

8. The module of claim 7 wherein said sensor is an electrochemical sensor.

9. The module of claim 7 wherein said sensor is an optical sensor.

10. The module of claim 7 wherein said sensor is an electrochemical sensor.

11. The module of claim 1 wherein said module is a microfluidic analyzer module.

12. The module of claim 7 further including a fourth layer overlying said third polyimide sheet, said fourth layer providing a concave surface in operative association with said valve region.

13. The module of claim 12 wherein said valve actuator comprises a pressure source communicating with said concave surface portion.

14. The module of claim 1 wherein said channels are up to approximately 0.015" wide and up to approximately 0.015" deep.

* * * * *